United States Patent [19]

Shibano et al.

[11] 4,403,511

[45] Sep. 13, 1983

[54] HYDRAULIC VIBRATION TESTER

[75] Inventors: Makoto Shibano, Hatano; Hideaki Kakuma, Atsugi; Hisatake Yasuyama, Zama, all of Japan

[73] Assignee: Kabushiki Kaisha Akashi Seisakusho, Tokyo, Japan

[21] Appl. No.: 308,478

[22] Filed: Oct. 5, 1981

Related U.S. Application Data

[63] Continuation-in-part of Ser. No. 136,546, Apr. 2, 1980, abandoned.

[30] Foreign Application Priority Data

Apr. 13, 1979 [JP] Japan .................................. 54-45616

[51] Int. Cl.³ ............................................. G01N 29/04
[52] U.S. Cl. ..................................................... 73/665
[58] Field of Search ........................................... 73/665

[56] References Cited

U.S. PATENT DOCUMENTS 2,773,482 12/1956 Dickie ................................ 73/665
2,865,173 12/1958 Dickie ................................ 73/665

*Primary Examiner*—Anthony V. Ciarlante
*Attorney, Agent, or Firm*—Robert E. Burns; Emmanuel J. Lobato; Bruce L. Adams

[57] ABSTRACT

A hydraulic vibration tester comprises an actuator comprising a piston reciprocable in a cylinder connected with a vibration testing table and a direct drive type servo valve for supplying pressure fluid alternately to opposite ends of the cylinder. The servo valve comprises a spool valve member reciprocable in the bore of a valve body by a magnetic coil supplied with alternating current and located in a direct current magnetic field. At opposite ends of the spool valve member there are coned disc springs acting to bias the spool valve member to a median position and acting to allow only an axial reciprocating movement of the spool valve member at a frequency in the range of 650 Hz to 2000 Hz. The passages connecting the servo valve with the activator have a resonant frequency in the same range so as to achieve an effective vibration test in the high frequency range.

8 Claims, 5 Drawing Figures

HYDRAULIC VIBRATION TESTER

REFERENCE TO PRIOR APPLICATION

This application is a continuation-in-part of our application Ser. No. 136,546 filed Apr. 2, 1980 now abandoned.

FIELD OF INVENTION

This invention relates to a hydraulic vibration tester device in which a vibromotive force may be produced through the medium of force applied by liquid such as oil, and more particularly to a hydraulic vibration tester device allowing to perform a vibration test by enabling the production of the rate vibromotive force up to a high frequency range of about 2,000 Hz.

BACKGROUND OF THE INVENTION

It is well known in the art that a frequent application of a conventional type of hydraulic vibration tester device is found in a component element fatigue test in reference to a sine wave form in a low frequency range due to the fact that a high output or a high amplitude may easily be produced of a low cost compared with that of electrically operated vibration testers.

However, the most popular servo valve is of a nozzle flapper type and also the most popular type of a hydraulic vibrating machine is one having this kind of servo valve. Thus, in case of this kind of vibrating machine, it is found that an upper limit of the working frequency is a low frequency of about 200 to 300 Hz due to structural restrictions of the nozzle flapper. As special testing equipment, a hydraulic vibrating machine having a direct drive type servo valve may also be applied in a frequency range of 500 to 650 Hz. However, this type of testing equipment has the disadvantage that the transmitted force is decreased in reverse proportion to the square of the number of vibrations, as shown in FIG. 1, when the resonance frequency $f_n$ (500 to 650 Hz) of the tester device is exceeded. The resonance frequency $f_n$ is thus the practical upper limit of the working frequency range of the tester device, resulting in that a conventional type of a hydraulic vibrating tester device may not be used in a higher frequency range higher than about 500 to 650 Hz.

SUMMARY OF THE INVENTION

This invention aims at resolving the disadvantages described above and has as its object the provision of a hydraulic vibrating test device in which a vibration test may be performed even in a high frequency range (for example, an upper limit of about 2,000 Hz) in which a conventional type of tester may not be used, by forming a locally effective operation range.

Therefore, the hydraulic vibration tester device of the present invention is provided with an actuator comprising a piston fitted in a cylinder and a vibration testing table member connected to the piston through a rod, and with a direct drive type servo valve enabling an alternative feeding of working fluid at opposite ends of the cylinder of said actuator through passages so as to reciprocate said piston, and is characterized in that each of the resonance frequency range of the servo valve and the resonance frequency range of said passages is set to be a high frequency range so as to achieve a local effective working range in a high frequency range of said vibration testing table member as said piston is reciprocated.

BRIEF DESCRIPTION OF DRAWINGS

Referring now to the drawings wherein.

DESCRIPTION OF A PREFERRED EMBODIMENT

Figure 2:
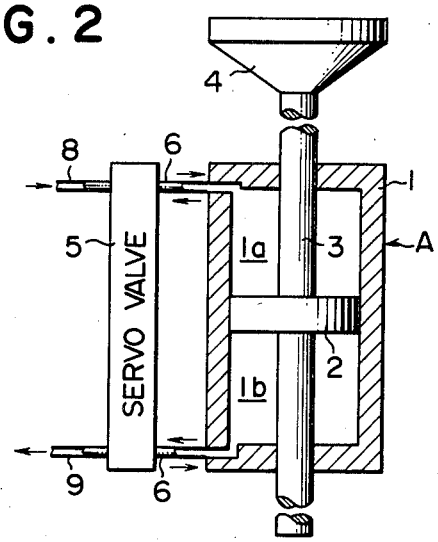
FIG. 2 is a schematic illustration of the structure of a hydraulic vibrating tester device of one preferred embodiment of the present invention.

As shown in FIG. 2, a piston 2 is fitted in a cylinder 1 of an actuator A, and a vibrating tester table member is connected to the piston 2 through a piston rod 3.

The actuator A is provided with a direct drive type servo valve 5 permitting an alternative feeding of the working pressure fluid under a high frequency to opposite ends of the cylinder 1, i.e. adjacent end wall surfaces of first and second hydraulic chambers 1a and 1b separated by the piston 2 in the cylinder, whereby the piston 2 may be reciprocated and resulting in that the vibrating tester table member 4 may be vibrated or oscillated.

Figure 1:
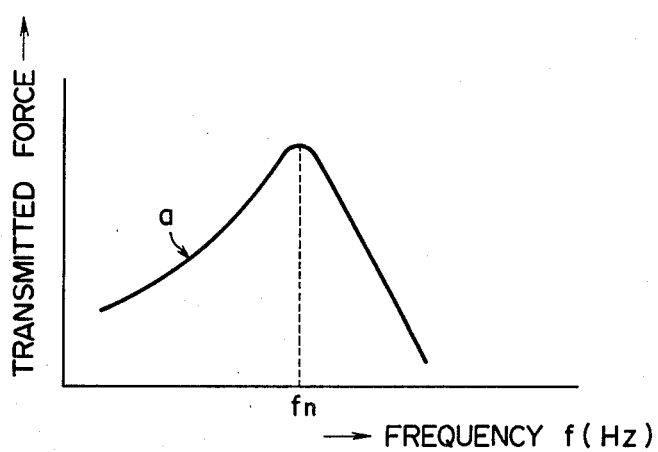
FIG. 1 is a graph for illustrating the operation of a conventional hydraulic vibrating tester device.
Figure 3:
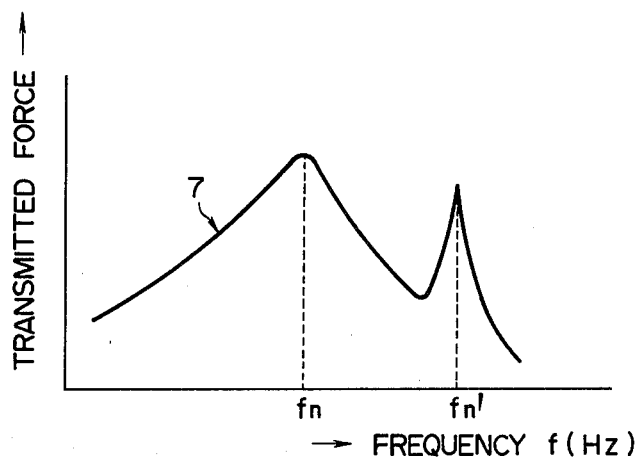
FIG. 3 is a graph illustrating the operation of the hydraulic vibrating tester device.

When it is assumed that the cross section of the passage 6 connecting the cylinder 1 with the servo valve 5 is defined as S, the effective length of the passage 6 is defined as l, and the mean volume of both of the hydraulic chambers 1a and 1b at opposite sides of the piston 2 in the cylinder 1 is defined as V, a condition for the working fluid to have a resonance in the actuator A may be expressed as follows in reference to the Helmholtz's principle of a resonator, when the frequency of resonance is $f_n'$:

$$f_n = \frac{C}{2\pi} \frac{S}{V \cdot l} \qquad (1)$$

where, C is a constant,

Therefore, it is possible to have a characteristic of resonance of the tester device as shown in FIG. 3 at 7 and further to achieve a local effective working range in such a higher frequency range than that of the conventional tester device (the upper limit is 1,500 to 2,000 Hz) when the cross sectional area S and the effective length l of the passage 6 as well as the mean volume V of the hydraulic chamber are defined in such a way that the resonance frequency $f_n'$ is higher than the resonance frequency $f_n$ found in the conventional type of the tester device shown in FIG. 1.

That is, in the present invention, each of the values S, l and V is defined in such a manner that the relation of $f_n' > f_n$ is fulfilled.

In other words, each of the resonance range of the servo valve 5 and the resonance range in the passage 6 is reached in said high frequency range so as to achieve a local effective operating range in a high frequency range of the vibration tester table member 4 as the piston 2 is reciprocated.

The reason why the resonance range of the servo valve 5 is set in said high frequency range is that if the operation range of the servo valve 5 is a low frequency range, an overall working range of the tester device is restricted by the operation range of the servo valve 5 even if the resonance range in the passage is increased, and resulting in that the device may be operated only at a low frequency range.

Figure 4:
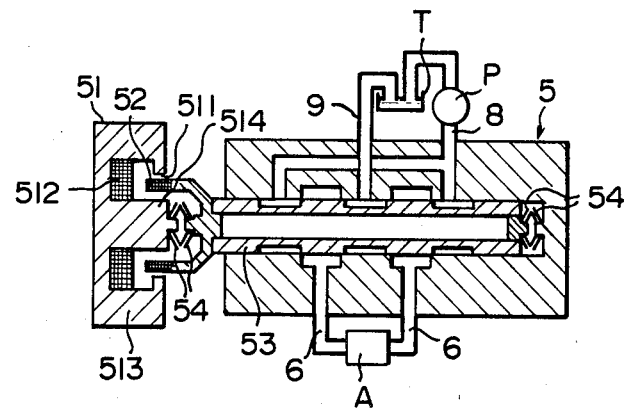
FIG. 4 is a sectional view showing a direct drive servo valve.

Due to this fact, the direct drive type servo valve 5 has such a structure as shown in FIG. 4.

That is, the direct drive type servo valve 5 is, as shown in FIG. 4, provided with a magnetic field generating structure 51 having a gap 511 for enabling the production of a magnetic field, a spool-valve-driving coil member 52 fitted in the gap 511 and reciprocated therein, and with a hollow light spool valve 53 fixed to the coil member 52. Opposed coned disc springs 54 for supporting the spool valve member 53 are fitted between both ends of the spool valve member 53 and the main body part so as to allow only an axial reciprocating movement of the spool valve member 53 in said high frequency range. It will be seen that at each end of the spool valve 53, there are two coned disc springs 54 disposed face-to-face coaxially with the spool valve 53.

The magnetic field generating structure 51 is constituted by an energizing coil 513 and a pole piece 514, and an annular gap 511 is formed between the yokes 513 and the pole piece 514. Therefore, when DC electric current is fed to the energizing coil 512, a DC magnetic field is produced in the gap 511. Hence when AC electric current is fed to the coil member 52 from a power supply not shown, an electro-magnetic force is generated under a cooperative action with the magnetic field in the gap 511 so as to reciprocate the coil member 52 and the spool valve member 53.

Figure 5:
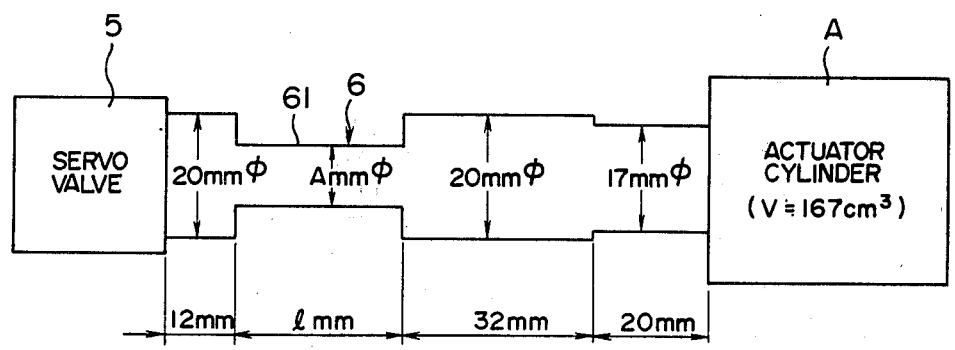
FIG. 5 is a schematic illustration showing the shape of one of the passages in the servo valve.

The passage 6 is constituted by a plurality of passage sections having a different effective cross sectional area which are connected in series with each other, for example, as shown in FIG. 5, in such a way that the resonance range is set in said high frequency range. In FIG. 5, only one of the two passages 6 is illustrated, the other passage having the same shape as that of the illustrated passage.

The bulk modulus k of a pipe can be expressed by the following equation:

$$k = (bE/2a)$$

in which
E: Longitudinal bulk modulus of the pipe.
a: Inner radius of the pipe.
b: Wall thickness of the pipe.

However, the fluid passages 6, as illustrated in FIG. 4, are not of a pipe form but rather passages in the iron block, so that they will have a higher bulk modulus than indicated by the above equation.

The following table illustrates an example in which the size of the passage section 61 of the passage 6 is properly modified to change the resonance frequency $f_n'$.

| Effective Sectional Area A (mm$\phi$) | Resonance Frequency $f_n$ (Hz) |
|---|---|
| 4 | 800 |
| 8 | 1,500 |
| 13 | 1,800 |

Provided that the length of the passage 1 is 50 mm.

Mechanical resonances of the spool valve member 53, the servo valve 5 and the coned disc springs 54 are set, as described above, between 1,500 and 2,000 Hz. However, it has been found that when the resonance frequency $f_n'$ of the passage 6 is approximately the same value, a rate of transmittance of the force up to 2,000 Hz may effectively be accommodated.

In order to improve a conventional type of a vibration tester device to make a device of the present invention, the cross sectional area S of the passage 6, i.e. the diameter of the passage is modified.

Further, even if the effective length of the passage 6 is modified under the provision of a passage having a proper length, the conventional type of the device may be modified to the device of the present invention.

In turn, a hydraulic pump P is connected to the working fluid in-flow passage 8 shown in FIG. 2 and FIG. 4. The hydraulic pump P is driven to feed the working fluid stored in the oil tank T into one of the hydraulic chambers 1a and 1b in the actuator A through the inflow passage 8 and the servo valve 5, then the oil is returned back to said oil tank T from the other hydraulic chambers 1b or 1a in the actuator A through the servo valve 5 and the out-flow passage 9.

As the working fluid, a petroleum-based oil may usually be applied, and for example, TELUS-33 manufactured by Shell Sekiyu K.K. or Mobile DTE 26 (both are trademarks) may be used. The bulk modulus of the working fluid varies slightly but a value about $\beta = 1.4 \times 10^4$ kg/cm$^2$ is preferable. However, this value may be varied if the hydraulic pressure of the working fluid is varied or if some air bubbles are mixed in the hydraulic oil. Our experiments have shown that a variation of $\beta = 1.2$ to $1.5 \times 10^4$ kg/cm$^2$ may be found. A standard value of the pressure of the working fluid is set at 210 kg/cm$^2$. However, even if a pressure less than the standard value is set, the device of the present invention may be operated with only the vibration force being decreased.

As described in detail hereinbefore, in accordance with the hydraulic vibration tester device of the present invention, since each of the resonance range of the servo valve 5 and the resonance range of the passage 6 is set in a high frequency range so as to form a local effective working range in said high frequency range of the vibration tester table member 4 as the piston 2 is reciprocated, it is possible to have an effective generation of a resonance phenomenon with the working fluid in the cylinder 1 being used as a spring and the piston 2 being applied as a mass, in a high frequency range (resonance frequency $f_n'$; $f_n' > f_n$) higher than the resonance frequency $f_n$ of a conventional type of device. Therefore, the present invention has such an advantage as a hydraulic vibration tester device which has only been allowed to be used in a low frequency range may generally be applied if the device is used in a local frequency range in such a high frequency range as described above.

What is claimed is:

1. Hydraulic vibration tester provided with an actuator comprising a piston fitted in a cylinder and a vibration testing table member connected to the piston through a piston rod and with a direct drive type servo valve enabling an alternative feeding of working pressure fluid alternately to opposite ends of the cylinder of said actuator through passages so as to reciprocate said piston, characterized in that each of the resonance frequency range of said servo valve and the resonance frequency range of said passages is set to be in a high frequency range above 650 Hz so as to achieve a local effective working range in a high frequency range above 650 Hz of said vibration testing table member as said piston is reciprocated.

2. Hydraulic vibration tester as set forth in claim 1, wherein the upper limit of said high frequency range is about 1,500 to 2,000 Hz.

3. Hydraulic vibration tester as set forth in claim 1, wherein said servo valve comprises a valve body having a bore into which said passages open, a spool valve member reciprocable in said bore, a magnetic coil member fixed to one end of said spool valve member and a magnetic field generating structure having a gap in which a magnetic field is produced and in which said magnetic coil member is received and coacts with said magnetic field to reciprocate said spool valve member, and spring means fitted between both ends of said spool valve member and said valve body to allow only an axial reciprocating movement of said spool valve member in said high frequency range.

4. Hydraulic vibration tester as set forth in claim 3, wherein said spring means comprises coned disc springs disposed coaxially between the ends of said spool valve member and said valve body.

5. Hydraulic vibration tester as claimed in claim 4, wherein said spring means at each end of said spool valve body comprises two coned disc springs disposed face-to-face with their peripheries engaging one another.

6. Hydraulic vibration tester as claimed in claims 4 or 5, wherein said magnetic coil member is annular and said spring means at one end of said spool valve member is disposed inside said magnetic coil member.

7. Hydraulic vibration tester as set forth in claim 3, wherein said passages are formed primarily in said valve body.

8. Hydraulic vibration tester as set forth in claim 1, wherein said passages have a plurality of passage sections connected in series with each other having different effective cross sectional areas so as to expand said high frequency working range of said actuator.

* * * * *